United States Patent [19]

Haswell

[11] 4,076,017
[45] Feb. 28, 1978

[54] POSTPARTUM FLUID LOSS RECEPTACLE

[76] Inventor: John N. Haswell, 607 Dubois St., Vincennes, Ind. 47591

[21] Appl. No.: 657,161

[22] Filed: Feb. 11, 1976

[51] Int. Cl.$^2$ .................... A61B 10/00; A61B 19/06
[52] U.S. Cl. ........................ 128/2 F; 128/132 D; 128/292
[58] Field of Search ............ 128/2 F, 132 D, 292, 128/283, 295

[56] References Cited

U.S. PATENT DOCUMENTS

| 1,143,046 | 6/1915 | Gilmore | 128/292 |
|---|---|---|---|
| 1,597,556 | 8/1926 | Townsend | 128/292 |
| 3,030,957 | 4/1962 | Melges | 128/292 |
| 3,199,507 | 8/1965 | Kamm | 128/292 X |
| 3,386,444 | 6/1968 | Brenner et al. | 128/292 |
| 3,452,750 | 7/1969 | Blanford | 128/292 X |
| 3,494,356 | 2/1970 | Melges | 128/292 X |
| 3,646,938 | 3/1972 | Haswell | 128/292 |
| 3,769,971 | 11/1973 | Collins | 128/132 D |

*Primary Examiner*—Kyle L. Howell
*Attorney, Agent, or Firm*—Woodard, Weikart, Emhardt & Naughton

[57] ABSTRACT

A postpartum fluid loss receptacle is disclosed herein comprising a sheet which is positioned beneath the patient. The receptacle includes a pocket formed by folding an edge of a non-absorbent sheet upon itself and sealing it together. The pocket collects the fluid and includes graduations to permit measurement of the amount of the fluid.

3 Claims, 7 Drawing Figures

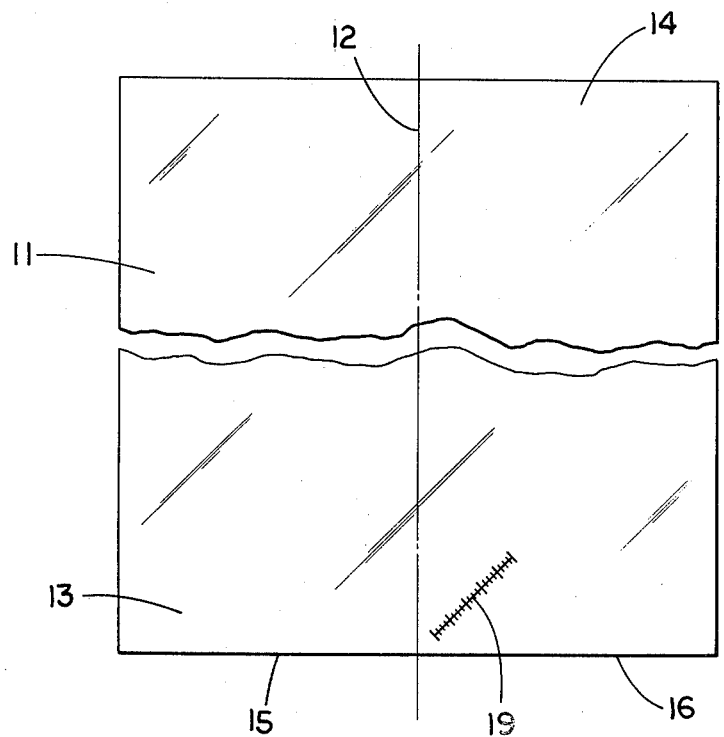
Fig. 1
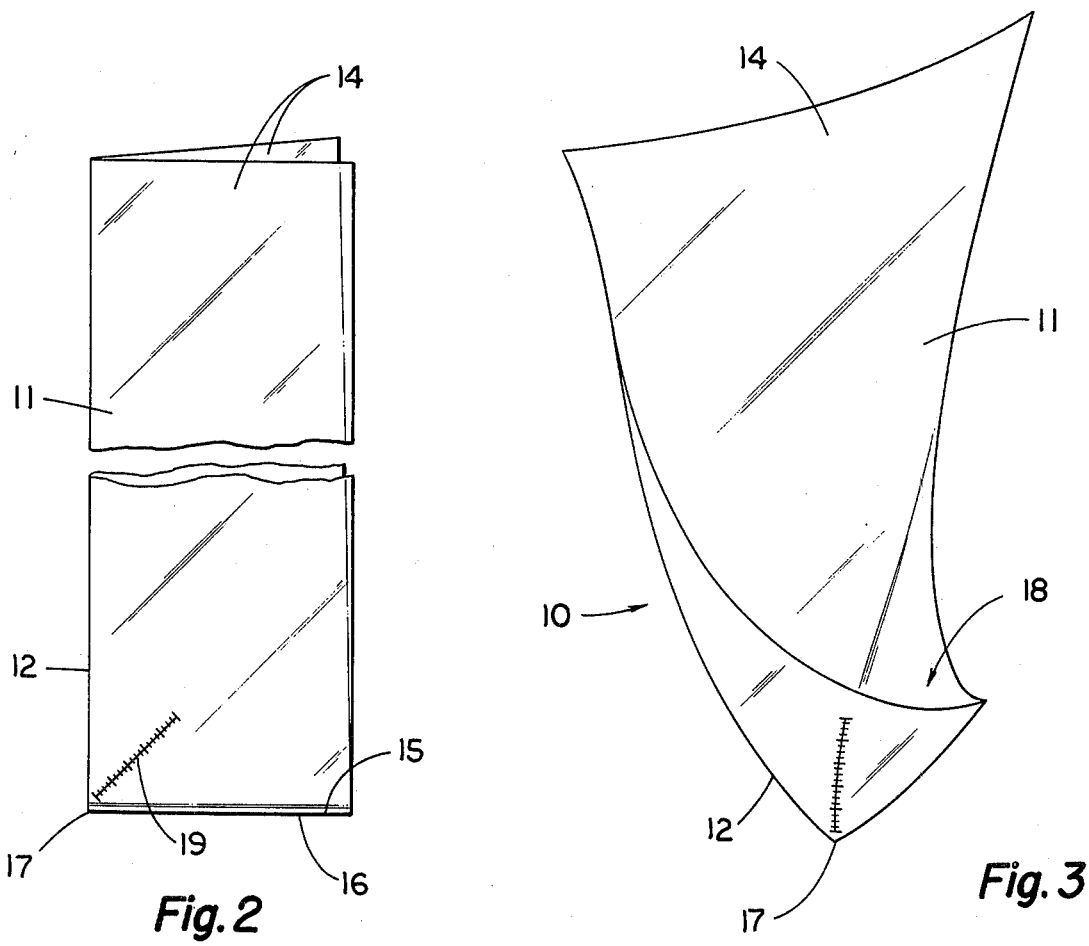
Fig. 2
Fig. 3

POSTPARTUM FLUID LOSS RECEPTACLE

BACKGROUND OF THE INVENTION

1. Field of the Invention

This invention relates to receptacles for collecting and measuring the amount of postpartum fluid loss.

2. Description of the Prior Art

Surgical drapes are customarily used in operating rooms. The drapes protect the surgically prepared areas of the skin from contamination. Unprepared portions of the skin and of the room are also isolated by the drapes from the prepared areas, thereby reducing the potential for contamination due to these sources.

Surgical drapes are also employed in a delivery room when a women gives birth to a child. During delivery, the woman will lose a significant amount of amniotic fluid and blood. It is desirable that these fluids be collected to protect the delivery table and surrounding areas from being unduly soiled. Additionally, collection of these fluids permits the physician to determine the proper treatment of the mother, and to evaluate the mother's speed of recovery. Present surgical drapes do not permit the postpartum fluids to be readily and totally collected and readily measured.

A method and device for collecting and measuring postpartum blood loss is disclosed in my U.S. Pat. No. 3,646,938, issued on Mar. 7, 1972. The device therein disclosed comprises a substantially flat, pliable sheet. The sheet is placed beneath the buttocks of the patient, and the blood lost is collected thereon. When held pendantly, the sheet causes the blood to pool and graduations on the sheet permit measurement of the blood collected to be made. The device and method of this previous patent do permit collection and measurement of postpartum blood loss. One aspect of the present invention, however, is the provision of an improved device of the type described in my previous patent, the improvement facilitating increased accuracy in the measurement of the amount of blood collected.

SUMMARY OF THE INVENTION

A postpartum fluid loss receptacle is disclosed herein which comprises a first elongated sheet of flexible material that is essentially nonabsorbent to body fluids, the first sheet having a first end portion forming a first pocket and a second end portion, the first end portion of the first sheet being folded and defining a first edge and a second edge, the edges having a common point, the first edge being sealingly attached to the second edge continuously along a line extending from the common point.

It is an object of the present invention to provide a postpartum fluid loss receptacle which is easily used and fully collects the lost fluids.

An additional object of this invention is to provide a postpartum fluid loss receptacle which is easily constructed and is inexpensive.

Another object of the present invention is to provide a postpartum fluid loss receptacle which protects against contamination and prevents the delivery table and room from becoming soiled.

A further object of the present invention is to provide a postpartum fluid loss receptacle which permits the amniotic fluid and the blood to be collected separately.

It is yet another object of this invention to provide a postpartum fluid loss receptacle which enables the volume of fluids collected to be readily determined.

Further objects and advantages of the present invention will become apparent from the description and figures which follow.

BRIEF DESCRIPTION OF THE DRAWINGS

FIG. 1 is a top view of material utilized in constructing an embodiment of the receptacle of the present invention.

FIG. 2 is a top view of the material of FIG. 1 with one side folded against the other side.

FIG. 3 is a perspective view of an embodiment of the receptacle of the present invention.

DESCRIPTION OF THE PREFERRED EMBODIMENTS

Figure 4:
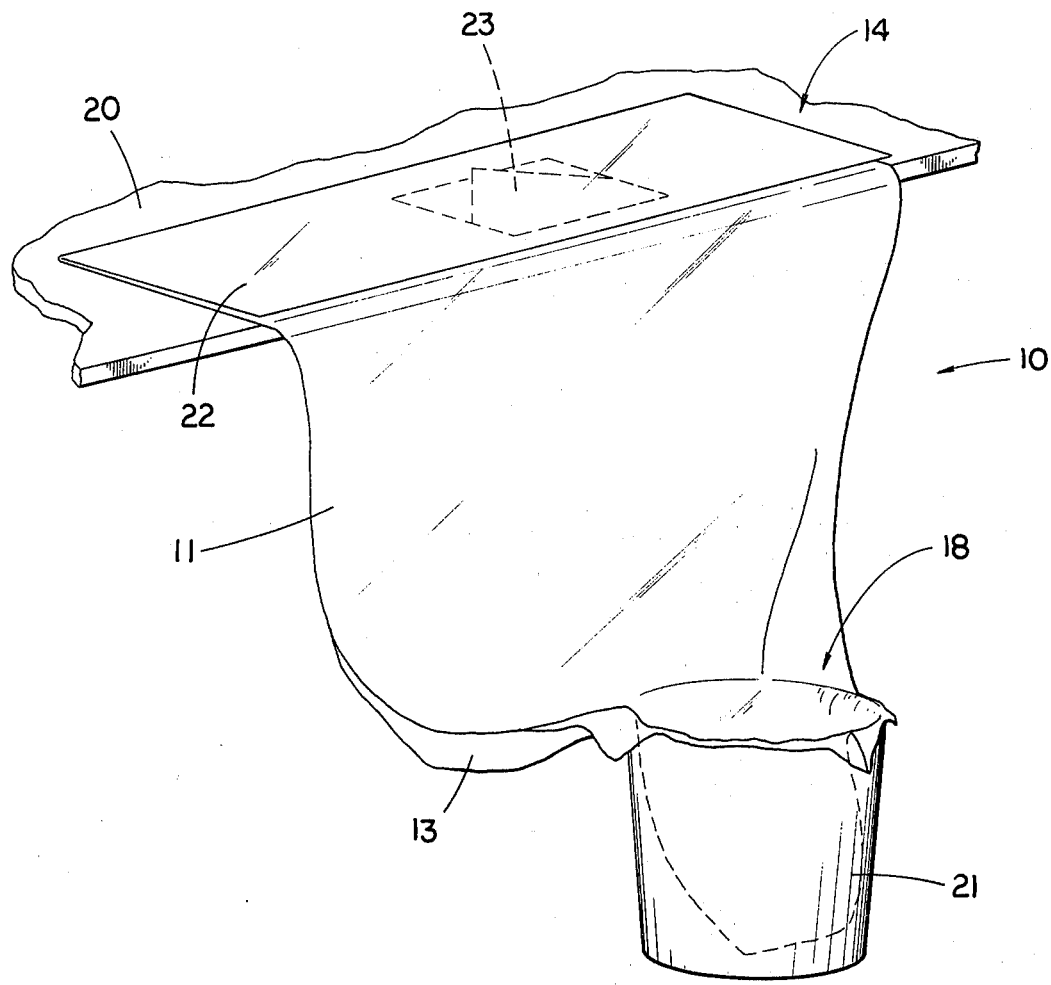
FIG. 4 is a perspective view of a second embodiment of the receptacle of the present invention having the second end portion upon a delivery table and the first pocket supported in a rigid receptacle.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The postpartum fluid loss receptacle of the present invention provides a simple and efficient means for collecting and measuring the amount of fluids lost by a woman in conjunction with giving birth to a child. The material from which the receptacle is constructed must therefore be suitable for surgical use. Primarily, the material should be aseptic and should be easily manipulated by the persons attending the woman during and after childbirth.

A second requirement of the material comprising the present receptacle is that it have sufficient flexibility and strength. The material should be flexible or pliable to permit the receptacle to be folded for transportation and storage. At the same time, the materials should be strong enough to support the weight of the fluids which will be collected therein. The present receptacle is designed primarily to collect the amniotic fluid and the blood which is lost during and subsequent to childbirth. These fluids may be collected together or separately, as will be explained further with reference to the figures.

Referring in particular to FIGS. 1-3, there is shown one embodiment of the receptacle according to the present invention. The receptacle 10 comprises a flexible sheet 11 which includes a first end portion 13 and a second end portion 14. The material is preferably a transparent plastic, and should be essentially nonabsorbent to body fluids. The sheet 11 is folded along the longitudinal center line 12, the folded first end portion defining a first edge 15 and a second edge 16. The first edge 15 is sealingly attached to the second edge 16 along a line extending from the common point 17. The seam between first edge 15 and second edge 16 may have any shape but is most conveniently a straight line. The second edge end portion is then opened up to be flat, and the first end portion forms a pocket 18.

Graduations 19 are included at the first end portion along the side of pocket 18 to indicate the volume of material contained within the pocket 18. The graduations may correspond to any measuring system, but preferably indicate the volume in cubic centimeters or milliliters. The graduations should read at least as high as 500 cubic centimeters, and indications at every 50 cc are appropriate.

The positioning of the receptacle 10 for its intended use is depicted in FIG. 4. The second end portion 14 is positioned upon the delivery table 20, and the first end portion 13 is suspended over the side of the table. The patient is positioned to have her buttocks upon the second end portion 14, and the weight of the patient acts to hold the second end portion 14 upon the table 20. A rigid receptacle 21 is positioned on the floor of the delivery room to support the pocket 18. The "kick bucket" which is generally found in a delivery room may be used for this purpose.

Figure 5:
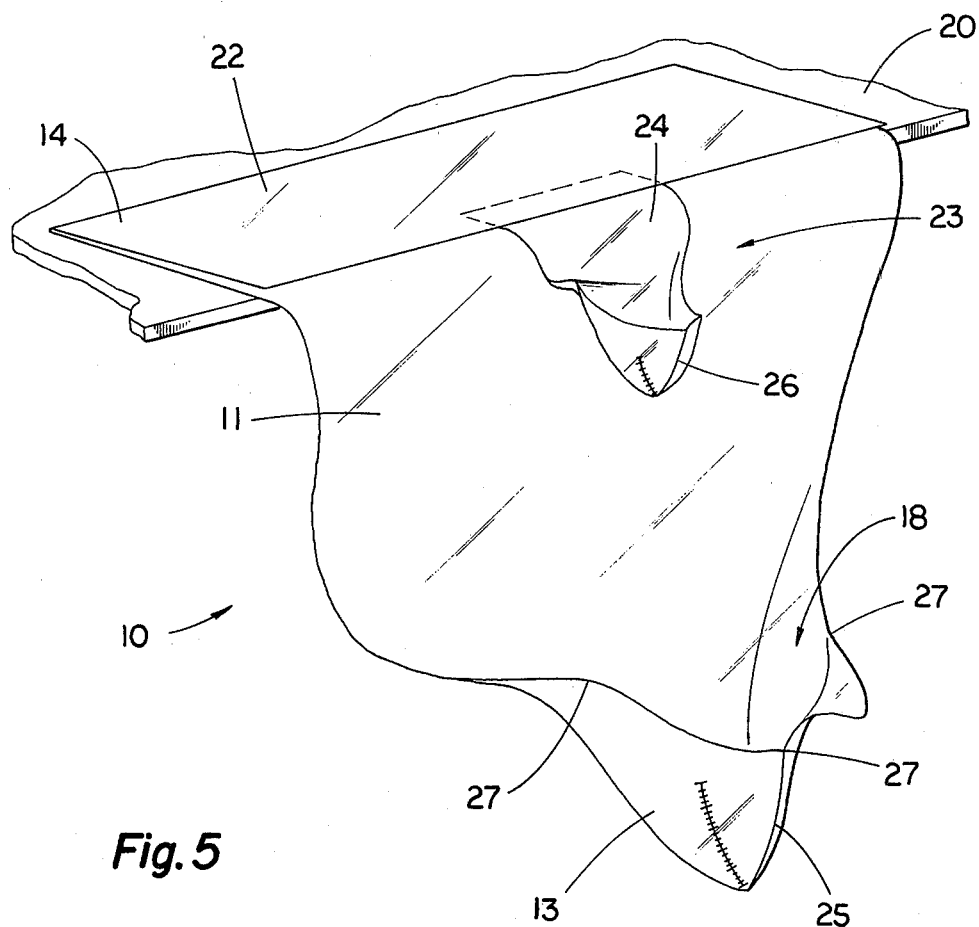
FIG. 5 is a perspective view of the receptacle of FIG. 4 with the second pocket opened.

An embodiment of the present invention having two pockets is depicted in FIGS. 4 and 5. The second end portion 14 of sheet 11 includes a flap 22 which spans the full width of sheet 11 and extends in the direction of the first end portion 13. A second pocket 23 is attached to the second end portion 14 beneath the flap 22.

Second pocket 23 comprises a flexible sheet 24. Preferably the material is the same as the material of sheet 11, and it should at least be nonabsorbent to body fluids. Because the second pocket 23 is not as large as pocket 18, the strength requirements of the material of sheet 24 are not as great. The pocket 23 is formed in the identical manner as is pocket 18. Sheet 24 includes a first end portion which is folded over upon itself and two adjacent edges are sealingly attached to form seam 26.

The second pocket 23 has a first position in which it is folded under the flap 22, as is shown in FIG. 4. The second pocket 23 may be unfolded and opened up as is shown in FIG. 5.

The embodiment incorporating two pockets is used in much the same manner as previously described for the receptacle having one pocket. The second end portion 14 is positioned on the delivery table 20, and the patient is positioned with her buttocks upon the second end portion 14. The receptacle 10 initially has the second pocket 23 folded under the flap 22, as shown in FIG. 4. The receptacle 10 is maintained in this configuration while primarily the amniotic fluid is collected in the pocket 18. At the appropriate time, the second pocket 23 is unfolded from the flap 22 and blood lost by the patient is collected therein.

As is particularly shown in FIG. 5, the present construction of the pockets naturally causes them to be in the open, receiving position when suspended from the edge of the delivery table 20. The weight and increased rigidity of the seams 25 and 26 causes the fronts of the pockets to remain displaced from the backs. This avoids the necessity of certain prior devices which required additional apparatus be employed to maintain the pockets in the open position. The present receptacle achieves this result while being easily and inexpensively constructed.

Figure 6:
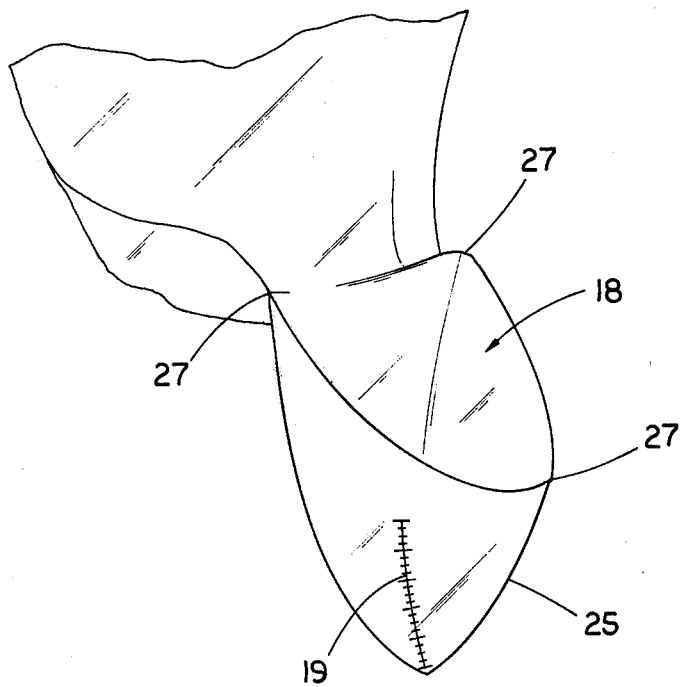
FIG. 6 is a perspective view of the first pocket of the receptacle of FIG. 5 being held pendantly.
Figure 7:
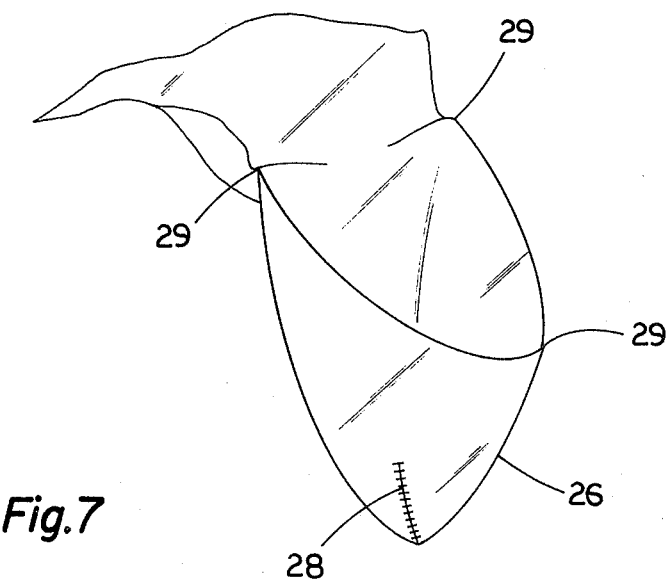
FIG. 7 is a perspective view of the second pocket of the receptacle of FIG. 5 being held pendantly.

The body fluids are collected in the respective pockets as described previously. The amount of fluid contained in each of the pockets is then determined in an identical manner. The pockets are held pendantly, as is best shown in FIGS. 6 and 7, and the amount of fluid contained therein is read directly by aid of the graduations 19.

The second pocket 23 includes graduations 28 positioned analogous to graduations 19 of pocket 18. Second pocket 23 generally will be used to collect the blood lost by the patient. The amount of blood lost will generally be less than 250 cubic centimeters, and the graduations therefore preferably indicate in steps of 10 cc. to at least 250 cc. To determine the amount of blood collected within second pocket 23, the pocket is held pendantly and the amount is read directly by aid of the graduations 28.

The pockets 18 and 23 may include predetermined support points 27 and 29, respectively. The pockets are then preferably held pendantly by the support points when a determination of the amount of fluid collected is to be made. It is not necessary that the location of these points be specified, however, it being sufficient that the pockets be held pendantly in a manner which will cause the fluids to be retained and the volume thereof to be determined.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention and the scope of the claims are desired to be protected.

What is claimed is:

1. A postpartum fluid loss receptacle which comprises:
    a first sheet of flexible material that is essentially nonabsorbent to body fluids, said first sheet having a first end portion forming a first pocket and a second end portion, the first end portion of said first sheet being folded and defining a first edge and a second edge, the edges having a common point, the first edge being sealingly attached to the second edge continuously along a line extending from the common point; and
    a second pocket smaller than the first pocket, said second pocket being connected to and position relative said first sheet of flexible material between the first and second end portions.

2. The receptacle of claim 1 in which the second end portion of said first sheet includes a flap which extends in the direction of the first end portion of said first sheet, said second pocket being collapsible to be positioned beneath the flap.

3. A postpartum fluid loss receptacle which comprises:
    a first sheet of flexible material that is essentially nonabsorbent to body fluids, said first sheet having a first end portion forming a first pocket and a second end portion, the first end portion of said first sheet being folded and defining a first edge and a second edge, the edges having a common point, the first edge being sealingly attached to the second edge continuously along a line extending from the common point; and
    a second pocket smaller than the first pocket, the second end portion of said first sheet including a flap which extends in the direction of the first end portion of said first sheet, said second pocket being collapsible to be positioned beneath the flap, said second pocket comprising a second sheet of flexible material that is essentially nonabsorbent to body fluids, said second sheet having a first end portion and a second end portion, the first end portion of said second sheet being folded and defining a first edge and a second edge, the edges of said second sheet having a common point, the first edge of said second being sealingly attached to the second edge of said second sheet continuously along a line extending from the common point of the edges of said second sheet, said first end portion of said second sheet further including graduations to indicate the volume of material contained within said second pocket.

* * * * *

UNITED STATES PATENT AND TRADEMARK OFFICE
CERTIFICATE OF CORRECTION

PATENT NO. : 4,076,017
DATED : February 28, 1978
INVENTOR(S) : John N. Haswell

It is certified that error appears in the above–identified patent and that said Letters Patent are hereby corrected as shown below:

In column 5, line 7, after the word "second" and before the word "being" please add the word --sheet--.

Signed and Sealed this

Thirteenth Day of June 1978

[SEAL]

Attest:

RUTH C. MASON
Attesting Officer

DONALD W. BANNER
Commissioner of Patents and Trademarks